United States Patent [19]

Pesche

[11] Patent Number: 4,520,015

[45] Date of Patent: May 28, 1985

[54] METHOD FOR MANUFACTURING A PRODUCT FOR DESTROYING HARMFUL ANIMALS

[76] Inventor: Bernard Pesche, 4 Boulevard Diderot, 75012 Paris, France

[21] Appl. No.: 502,684

[22] Filed: Jun. 9, 1983

[30] Foreign Application Priority Data

Jun. 14, 1982 [FR] France ................ 82 10326

[51] Int. Cl.$^3$ ............... A01N 35/00; A01N 43/16; A01N 59/08; B01J 13/00
[52] U.S. Cl. ............... 424/153; 252/315.01; 252/315.3; 424/22; 514/779
[58] Field of Search ............ 252/315.01, 315.3; 424/22, 84, 333, 153, 331, 281

[56] References Cited

U.S. PATENT DOCUMENTS

| | | | |
|---|---|---|---|
| 2,420,308 | 5/1947 | Gates | 252/315.3 |
| 3,085,015 | 4/1963 | Schram | 252/315.3 X |
| 3,257,267 | 6/1966 | Hay | 162/159 |
| 3,854,981 | 12/1974 | Schon et al. | 427/212 |

FOREIGN PATENT DOCUMENTS

| | | | |
|---|---|---|---|
| 549318 | 7/1956 | Belgium . | |
| 1498299 | 9/1967 | France . | |
| 1575437 | 7/1969 | France . | |
| 348003 | 9/1960 | Switzerland . | |
| 762700 | 12/1956 | United Kingdom | 264/4 |
| 1163023 | 9/1969 | United Kingdom | 264/4.1 |
| 1180086 | 2/1970 | United Kingdom . | |

*Primary Examiner*—Richard D. Lovering
*Attorney, Agent, or Firm*—Wenderoth, Lind & Ponack

[57] ABSTRACT

Method for manufacturing products in the desired shape and ready for use for destroying harmful animals, by preparing a fluid, aqueous paste containing nutritive elements, at least one constituent which is toxic to the target animal, and a gelable constituent, putting the paste in the desired shape for the final product, gelling the paste, and preserving the gelled product thus obtained in a slightly acid, aqueous, saline medium or under a vacuum or an inert gas.

14 Claims, No Drawings

METHOD FOR MANUFACTURING A PRODUCT FOR DESTROYING HARMFUL ANIMALS

DESCRIPTION

The present invention relates to a method for manufacturing a product or bait for destroying harmful animals such as moles, muskrats and coypus, rats and small rodents, harmful mollusks, etc.

Failing a suitable method for manufacturing them, the prior art was limited to the criteria of composition, taste and odour for the baits, but the shape, the consistency, the volume and the humidity resistance of these baits were neglected. These features however play a very important part from the point of view of the attractiveness and effectiveness of the product.

An object of the invention is to overcome the aforementioned drawbacks and to provide a method for manufacturing a product which permits the reconstitution from natural food products of perfectly homogeneous complete foods, i.e. foods containing within their mass not only the usual nutritive elements for the target animal such as glucides, protides, lipides, mineral salts etc., but also preservatives, perfumes, attractive elements, colouring agents and toxic substances suitable for destroying the animals. The method further permits imparting to the products obtained a consistency, volume, shape and humidity which are as similar as possible to those of the usual food of each of the animals for which they are intended.

The invention therefore provides a method for manufacturing shaped products which are ready for use for destroying harmful animals, from a fluid aqueous paste containing the nutritive elements, at least one product which is toxic to the animal to be destroyed, and a gelable component, wherein the paste is put into the desired shape for the final product, the shaped paste is then gelled by putting the shaped product in contact with an aqueous solution of a metal salt capable of resulting in an exchange of ions with the gelable component, and the gelled product thus obtained is preserved in a slightly acid aqueous saline medium or under a vacuum or under an inert gas.

Further features and advantages of the invention will be apparent from the following description.

The method of the invention comprises the following successive steps:

(a) preparing a fluid aqueous paste containing the nutritive elements, at least one toxic product as concerns the animal to be destroyed, and a gelable constituent;
(b) putting the paste into the desired shape of the final product;
(c) gelling or setting into a mass the shaped paste; and
(d) preserving the gelled product.

The preparation of the aqueous paste comprises at least one of the following steps:

1. Putting the water soluble components and in particular the preservatives such as sodium benzoate, phenolated derivatives or esters of benzoic acid, formol, etc. into solution; an acidifying agent such as citric acid or ascorbic acid may also be added.
2. Putting chopped, ground or powdered nutritive elements in suspension in the aqueous solution; in practice this includes essentially glucides and protides.

The glucides comprise for example flours of cereals, gluten, root pulp, tubercules, fruits etc. and in particular carrots, beet roots, potatoes, etc.

The protides will be furnished for example by flours of animal origin (meat, fish, blood, etc.) or by mixed flesh (fish, meat, liver, butchers offals, etc.).

The relative proportions between the water and the aforementioned elements should be such that the mixture obtained is still very liquid.

3. Dispersing the binders and gelable agents.

While agitating, there is introduced into the product resulting from steps (a) and/or (b) a gelable constituent and, if desired, a binder. The gelable constituent is preferably an alkali metal alginate, such as sodium alginate. The proportion of sodium alginate will be preferably about 0.8 to 2% of the finished gelable product. The duration of the dispersion varies in accordance with the apparatus employed; it may be in particular about 10 minutes.

At this stage, it is possible to add binders such as carboxy-methyl-cellulose and its derivatives in the proportion of about 1 to 5% of the finished product.

It is also possible to introduce water miscible organic solvents in the solutions of alginates, and in particular alcohols such as ethanol, glycerol, glycol propylene, etc.

4. Emulsifying so as to, if desired, introduce oily products or products soluble in oil such as lipides in the form of vegetable or animal oils (coconut oil, colza, fish, cod, etc.).

Anti-oxidants soluble in oils and certain fillers may also be introduced.

The emulsification is carried out advantageously by means of emulsifiers such as poly-oxy-ethylenated derivatives of partial esters of fatty acids and anhydrides of hexitol (Tween 20, Tween 40), monolaurate, monopalmitate or monooleate or poly-oxy-ethylenated sorbitan, etc.

These emulsifiers are introduced generally in an amount representing 0.2 to 1.5% of the total weight of the product.

The toxic products will be introduced at any one of the aforementioned steps (1) to (4), depending on the nature of the poison employed and its solubility or non-solubility in water or oils. By way of examples of such products, there may be mentioned chlorophacinone, coumafene, metaldehyde, etc. Any toxic substance known for the destruction of the target animal may be employed.

This wide range of possibilities of the introduction of the poison and the various constituents of the gelable product constitutes one of the major advantages of the present invention.

As the product is at this stage in the form of a paste or a gel, the method of the invention then comprises putting the product into its final desired shape which is a function of the intended use. This shape will be, for example, a ball, a filament, a small earth worm, a large worm, a granule, a bead, a small noodle, a small shell-shaped product etc.

The desired shape is achieved preferably by means of an extrusion nozzle connected to a container containing the product and to an intermediate metering device which conveys to the nozzle the appropriate amount of product.

Depending on the shape of the nozzle, spherical or oblong products or ribbons of various width etc. may be obtained.

The shape and the dimensions of the end of the extrusion nozzle essentially determines the shape of the final bait.

Among the metering devices which may be employed, there may be mentioned by way of examples, peristaltic pumps, volumetric filling devices, and electropneumatic valves.

When the product is put into the desired final shape, the method comprises fixing the shape of this product by gelling it, i.e. setting its mass.

This gelling is achieved by the action of a gelling agent on the product containing the gelable constituent. The shaped product may be introduced into the gelling agent either by falling freely into a solution of the latter, or by direct introduction of the product emerging from the nozzle into a bath containing the gelling agent.

If the gelable constituent is an alginate, the gelling agent will be in particular an aqueous solution of a metal salt capable of achieving an exchange of ions with the gelable constituent.

As an example of a metal salt, there will be mentioned in particular calcium or aluminium salts (in particular the chlorides). If the salt is calcium chloride, it will be advantageously in the form of an aqueous solution containing 0.5 to 100 g per liter of the salt, a suitable dose being about 30 g per liter if the gelable constituent is sodium alginate.

When the product is gelled in this way and fixed in its final shape for intended use, it is necessary to ensure that it is preserved until use. For this purpose, the method of the invention comprises preserving the product in a slightly acid aqueous saline medium. Such a medium will be in particular constituted by an aqueous solution of sea salt containing a weak organic acid such as citric acid, lactic acid, etc. in an amount sufficient to ensure a slightly acid pH of about 6.5 to 7. This solution will contain advantageously the same gelling agent as that employed hereinbefore, in particular a calcium or aluminium salt, for example calcium chloride. In the brine, the sodium chloride will in particular be in a proportion of about 2 to 40% by weight and the calcium chloride 0.2 to 1% by weight.

The product may also be preserved in a vacuum or in an inert gas such as nitrogen, argon, etc.

The following non-limiting examples further illustrate the products according to the invention.

EXAMPLE 1

Product against muskrats and coypus in the form of doses having the shape of artificial fruits or legumes, whole or in pieces

| | |
|---|---|
| Cereal flour | 5.000% |
| Animal flour | 2.500% |
| Dehydrated lucezne | 20.000% |
| Vegetable oil | 10.000% |
| Emulsifier | 0.400% |
| Carboxy-methyl-cellulose | 0.500% |
| Sodium alginate | 2.000% |
| Sodium benzoate | 0.100% |
| Ascorbic acid | 0.040% |
| Gallates | 0.100% |
| Diatoma powder | 2.000% |
| Chlorophacinone | 0.005% |
| Attractive perfume | traces |
| Colouring agent | traces |
| Water to make up 100% | |

EXAMPLE 2

Product against moles in the form of worms

| | |
|---|---|
| Fish flesh | 23.000% |
| Blood flour | 4.000% |
| Animal oil | 8.000% |
| Carboxy-methyl-cellulose | 1.000% |
| Sodium alginate | 1.500% |
| Emulsifier | 0.500% |
| Benzoic acid esters in phenolic solution | 1.500% |
| Citric acid | 0.050% |
| Gallates | 0.100% |
| Sodium chloride | 1.000% |
| Inert filler | 1.750% |
| Coumafene | 0.025% |
| Colouring agent | traces |
| Attractive perfume | traces |
| Water to make up 100% | |

EXAMPLE 3

Product against rodents in the shape of balls, cubes, small plates, humbugs, small sausages or small blood sausages

| | |
|---|---|
| Cereal muslins | 30.000% |
| Blood flour | 3.000% |
| Oil | 9.000% |
| Sodium alginate | 1.750% |
| Emulsifier | 0.500% |
| Parahydroxybenzoic acid esters | |
| (Methyl sodium) | 0.600% |
| (Propyl sodium) | 0.300% |
| Citric acid | 0.040% |
| Gallates | 0.100% |
| Coumafene | 0.025% |
| Colouring agent | traces |
| Attractive anisated perfume | traces |
| Water to make up 100% | |

EXAMPLE 4

Product against harmful mollusks in the shape of granules, flakes, noodles or small shells

| | |
|---|---|
| Cereal muslins | 3.000% |
| Gluten | 0.500% |
| Dehydrated lucezne | 5.000% |
| Mineral salts | 1.000% |
| Carboxy-methyl-cellulose | 2.500% |
| Sodium alginate | 2.000% |
| Benzoic acid | 0.200% |
| Citric acid | 0.030% |
| Gallates | 0.080% |
| Metaldehyde | 5.000% |
| Fruit or vegetable perfume | traces |
| Colouring agent | traces |
| Water to make up 100% | |

With the method of the invention, it is possible to manufacture products perfectly suitable for the destruction of rodents (water rats, muskrats, coypus, etc.), moles, harmful mollusks (snails, arions, slugs, etc.), harmful birds etc.

Having now described my invention what I claim as new and desire to secure by Letters Patent is:

1. A method for manufacturing a product which is useful for destroying harmful animals, and which has approximately the shape and consistency of a natural food for the animal, which comprises the successive steps of:

providing a fluid, aqueous paste containing nutritive constituents, at least one constituent which is toxic to the animal, and a gelable constituent;

shaping said paste into a desired shape of the final product;

gelling said shaped paste by contacting said paste with an aqueous solution of a metal salt capable of achieving ion exchange with said gelable constituent; and preserving said gelled product in an acidic, aqueous, saline medium.

2. A method according to claim 1, wherein said fluid, aqueous paste is prepared by at least one of the following steps: (a) putting a water soluble preservative in solution in water, (b) putting nutritive elements consisting of glucides and protides in suspension, (c) dispersing the gelable constituent to which a binder is optionally added and (d) introducing, by emulsifying, a constituent soluble in oil, in the presence of emulsifying agents; the toxic constituent being introduced in one of the aforementioned steps based on its type and its solubility in the water or the oils.

3. A method according to claim 2, wherein the oil soluble constituent is a lipid.

4. A method according to claim 1, wherein the toxic constituent is toxic to a mole.

5. A method according to claim 1, wherein the gelable constituent is an alginate.

6. A method according to claim 5, wherein the alginate is an alkali metal alginate.

7. A method according to claim 5, wherein the alginate represents about 0.8 to 2% by weight of said paste.

8. A method according to claim 1, wherein the paste is put into the desired shape by passing metered amounts of said paste through a nozzle of suitable shape.

9. A method according to claim 1, wherein the gelable constituent is an alginate and the metal salt is a calcium salt.

10. A method according to claim 1, wherein the gelable constituent is an alginate and the metal salt is an aluminium salt.

11. A method according to claim 1, wherein the gelable constituent is an alginate and the metal salt is calcium chloride.

12. A method according to claim 1, wherein the gelable constituent is an alginate and the metal salt is aluminium chloride.

13. A method according to claim 1, wherein the aqueous solution contains 0.5 to 100 g of calcium chloride per liter.

14. A method according to claim 1, wherein the preservation is effected in an aqueous brine containing 2 to 40% by weight of sodium chloride, 0.2 to 1% by weight of a gelling metal salt and a sufficient amount of a weak acid so that the brine has a pH of between 6.5 and 7.

* * * * *